US00PP18012P2

(12) United States Plant Patent
Gray

(10) Patent No.: US PP18,012 P2
(45) Date of Patent: Sep. 11, 2007

(54) ***MANDEVILLA* PLANT NAMED 'WHITE VELVET'**

(50) Latin Name: ***Mandevilla* hybrid**
Varietal Denomination: White Velvet

(75) Inventor: John F. Gray, Hawthorne, FL (US)

(73) Assignee: Lake Area Nursery, Inc., Hawthorne, FL (US)

( * ) Notice: Subject to any disclaimer, the term of this patent is extended or adjusted under 35 U.S.C. 154(b) by 0 days.

(21) Appl. No.: 11/351,851

(22) Filed: Feb. 10, 2006

(51) Int. Cl.
*A01H 5/00* (2006.01)

(52) U.S. Cl. ..... Plt./232

(58) Field of Classification Search ..... Plt./232
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Mandevilla* plant named 'White Velvet', characterized by its upright vining growth habit; glossy, dark green-colored leaves; white-colored flowers faintly overlain with red purple with imbricate petals with ruffled margins; and tolerance to low and high temperatures.

2 Drawing Sheets

Botanical designation: *Mandevilla* hybrid.
Cultivar denomination: 'White Velvet'.

BACKGROUND OF THE INVENTION

The present Invention relates to a new and distinct cultivar of *Mandevilla* plant, botanically known as *Mandevilla* hybrid, and hereinafter referred to by the name 'White Velvet'.

The new cultivar is a product of a planned breeding program conducted by the Inventor in Hawthorne, Fla. The objective of the breeding program was to develop new *Mandevilla* cultivars with attractive flower form and coloration.

The new cultivar originated from a cross-pollination made by the Inventor in August, 2003, of the *Mandevilla* hybrid cultivar Red Velvet, disclosed in U.S. Plant Pat. No. 12,238, as the female, or seed, parent with an unnamed selection of *Mandevilla boliviensis,* not patented, as the male, or pollen, parent. The new *Mandevilla* was discovered and selected by the Inventor in a controlled environment in Hawthorne, Fla. on Apr. 12, 2005 from within the resultant progeny of the aforementioned cross-pollination. The new cultivar was selected on the basis of its unique flower coloration.

Asexual reproduction of the new cultivar by terminal cuttings in Hawthorne, Fla. since June, 2005, has shown that the unique features of this new *Mandevilla* are stable and reproduced true to type in successive generations.

SUMMARY OF THE INVENTION

Plants of the cultivar White Velvet have not been observed under all possible environmental conditions. The phenotype may vary somewhat with variations in environment such as temperature and light intensity without, however, any variance in genotype.

The following traits have been repeatedly observed and are determined to be the unique characteristics of 'White Velvet'. These characteristics in combination distinguish 'White Velvet' as a new and distinct cultivar:

1. Upright vining plant habit.
2. Vigorous growth habit.
3. Freely branching habit.
4. Large, glossy and dark green-colored leaves.
5. White-colored flowers that are faintly overlain with red purple with imbricate petals with ruffled margins.

Plants of the new *Mandevilla* can be compared to plants of the female parent, the cultivar Red Velvet. In side-by-side comparisons conducted in Hawthorne, Fla., plants of the new *Mandevilla* differed from plants of the cultivar Red Velvet in the following characteristics:

1. Plants of the new *Mandevilla* were more freely branching than plants of the cultivar Red Velvet.
2. Plants of the new *Mandevilla* and the cultivar Red Velvet differed in flower color as plants of the cultivar Red Velvet had dark pink to dark red-colored flowers.

Plants of the new *Mandevilla* can be compared to plants of the male parent selection. In side-by-side comparisons conducted in Hawthorne, Fla., plants of the new *Mandevilla* differed from plants of the male parent selection in the following characteristics:

1. Plants of the new *Mandevilla* had larger leaves than plants of the male parent selection.
2. Plants of the new *Mandevilla* had larger flowers than plants of the male parent selection.

Plants of the new *Mandevilla* can also be compared to plants of the *Mandevilla* cultivar, 'White Delite', disclosed in U.S. Plant Pat. No. 8,479. In side-by-side comparisons conducted in Hawthorne, Fla., plants of the new *Mandevilla* differed from plants of the cultivar White Delite in the following characteristics:

1. Plants of the new *Mandevilla* were more vigorous than plants of the cultivar White Delite.
2. Plants of the new *Mandevilla* had thicker stems than plants of the cultivar White Delite.
3. Plants of the new *Mandevilla* had larger leaves than plants of the cultivar White Delite.

4. Plants of the new *Mandevilla* had larger flowers than plants of the cultivar White Delite.
5. Plants of the new *Mandevilla* and the cultivar White Delite differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Mandevilla*.

The photograph on the first sheet comprises a side perspective view of a typical flowering plant of 'White Velvet'.

The photograph on the second sheet is a close-up view of typical flowers and leaves of 'White Velvet'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were about one year old and grown in one gallon containers in a polyethylene-covered greenhouse in Hawthorn, Fla. during the summer. During the production of the plants, day temperatures ranged from about 32° C. to about 35° C. and night temperatures were about 21° C.

Botanical classification: *Mandevilla* hybrid cultivar White Velvet.

Parentage:

*Female, or seed, parent.*—*Mandevilla* hybrid cultivar Red Velvet, disclosed in U.S. Plant Pat. No. 12,238.

*Male, or pollen, parent.*—Unnamed selection of *Mandevilla boliviensis,* not patented.

Propagation:

*Type.*—Terminal cuttings.

*Time to initiate roots, summer.*—About 14 days at 24° C.

*Time to initiate roots, winter.*—About 20 days at 21° C.

*Time to develop roots, summer.*—About 45 days at 32° C.

*Time to develop roots, winter.*—About 60 days at 12° C. to 27° C.

*Root description.*—Thick, fibrous.

*Rooting habit.*—Freely branching; moderately dense.

Plant description:

*Form.*—Perennial evergreen flowering plant; twining vine; initially upright, then vining, requires support to maintain upright habit. Plants are typically pinched about three months after planting to enhance lateral branch development; potentially two lateral branches form at every node.

*Plant height* (*length*).—About 30 cm.

*Plant diameter.*—About 28 cm.

*Vigor.*—Moderately vigorous.

*Lateral branches.*—Length: About 22 cm. Diameter: About 2.5 mm. Internode length: About 4 cm. Shape: Round in cross-section. Aspect: Initially upright, then trailing, requires support. Strength: Flexible, moderately strong. Texture: Developing stems; very fine white pubescence. Mature stems; woody and mostly smooth and glabrous. Color: Developing stems: 144A. Mature stems: Close to 148A overlain with close to 165A to 165B.

*Foliage description.*—Leaves simple, opposite; generally symmetrical and long-persisting. Length: About 15.2 cm. Width: About 5.3 cm. Shape: Elongated oblong. Apex: Sharply acute. Base: Cordate. Margin: Entire. Texture, upper and lower surfaces: Short fine pubescence. Luster: Upper surface, glossy; lower surface, somewhat glossy. Venation pattern: Pinnate. Petiole length: About 1.5 cm. Petiole diameter: About 2 mm. Petiole texture, upper and lower surfaces: Pubescent. Color: Developing and fully expanded foliage, upper surface: More green than 147A. Developing and fully expanded foliage, lower surface: Close to 146B. Venation, upper surface: Lateral veins, close to 147A; midvein, close to 146B. Venation, lower surface: Lateral veins, close to 146B; midvein, close to 146D. Petiole, upper surface: Close to 146A to 146B. Petiole, lower surface: Close to 146B to 146C.

Flower description:

*Flower type and habit.*—Simple salverfrom flowers arranged on axillary or terminal racemes; flowers face mostly outward. Flowers self-cleaning. Freely flowering, about 20 flowers per plant develop during the flowering season.

*Natural flowering season.*—Spring until frost in the autumn; flowering continuous.

*Flower longevity on the plant.*—About three to four days.

*Fragrance.*—None detected.

*Flowers.*—Appearance: Flared trumpet, corolla fused, five-parted; petals imbricate; flowers roughly star-shaped. Diameter: About 7.8 cm. Depth (length): About 5.4 cm. Corolla tube length: About 2.75 cm. Throat diameter: About 1.4 cm. Tube diameter, base: About 2.5 mm.

*Flower buds* (*just before opening*).—Length: About 4 cm. Diameter: About 6 mm. Shape: Elongated oblong. Color: Close to 155D faintly underlain with close to 61A.

*Corolla.*—Arrangement/appearance: Single whorl of five imbricate petals, fused into flared trumpet. Petal lobe length: About 3.4 cm. Petal lobe width: About 2.8 cm. Petal shape: Roughly spatulate. Petal apex: Rounded; undulate, ruffled appearance. Petal margin: Entire; undulate, ruffled appearance. Petal texture, upper and lower surfaces: Smooth, velvety. Color: Petal, upper surface, when opening: Close to 155D overlain with close to 61A. Petal, lower surface, when opening: Close to 155D faintly underlain with close to 61A. Petal, upper surface, fully opened; Close to 155D faintly overlain with close to 61A; color becoming closer to 155D with development. Petal, lower surface, fully opened: Close to 155D faintly underlain with close to 61A; color becoming closer to 155D with development. Tube, fully opened: Close to 150C. Throat, fully opened: Close to 4D.

*Sepals.*—Arrangement/appearance: Five per flower in a single whorl; fused; reflexed. Length: About 8 mm. Width: About 2 mm. Shape: Deltoid. Apex: Acuminate. Base: Fused. Margin: Entire. Texture, upper and lower surfaces: Smooth, glabrous; slightly waxy. Color, upper and lower surfaces: Close to 144D.

*Peduncles.*—Length: About 2.1 cm. Diameter: About 2 mm. Angle: Mostly straight. Strength: Flexible, but strong. Color: Close to 144A.

*Reproductive organs.*—Stamens: Quantity: Five; filaments fused to corolla. Anther shape: Oblong, elongated. Anther size: About 4 mm by 1.5 mm. Anther color: Close to 8C. Pollen: None observed. Pistils: Quantity: One. Pistil length: About 1.1 cm. Stigma shape: Rounded. Stigma color: Close to 150D. Style color: Close to 155D. Ovary color: Close to 144A to 144B.

*Seed/fruit.*—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to be tolerant to rain and wind and tolerant to temperatures from about 0° C. to about 40° C.

It is claimed:

1. A new and distinct cultivar of *Mandevilla* plant named 'White Velvet', as illustrated and described.

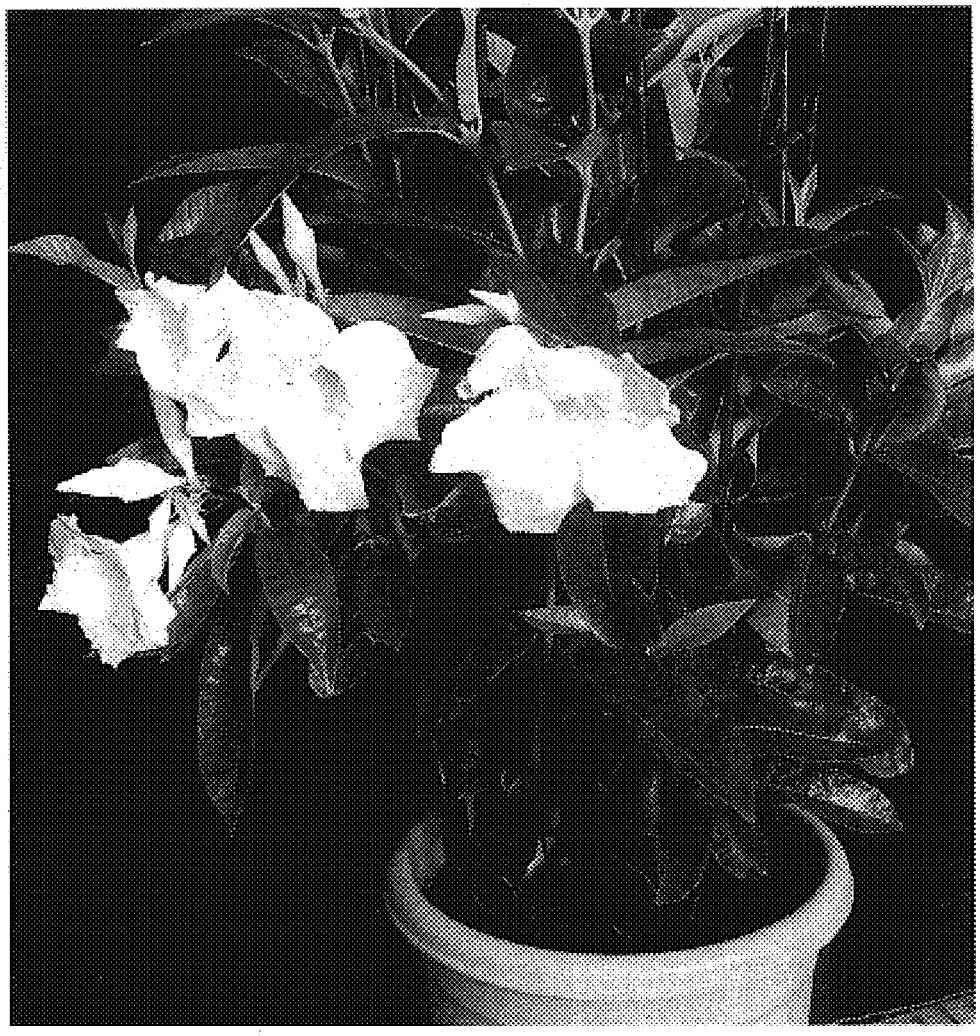

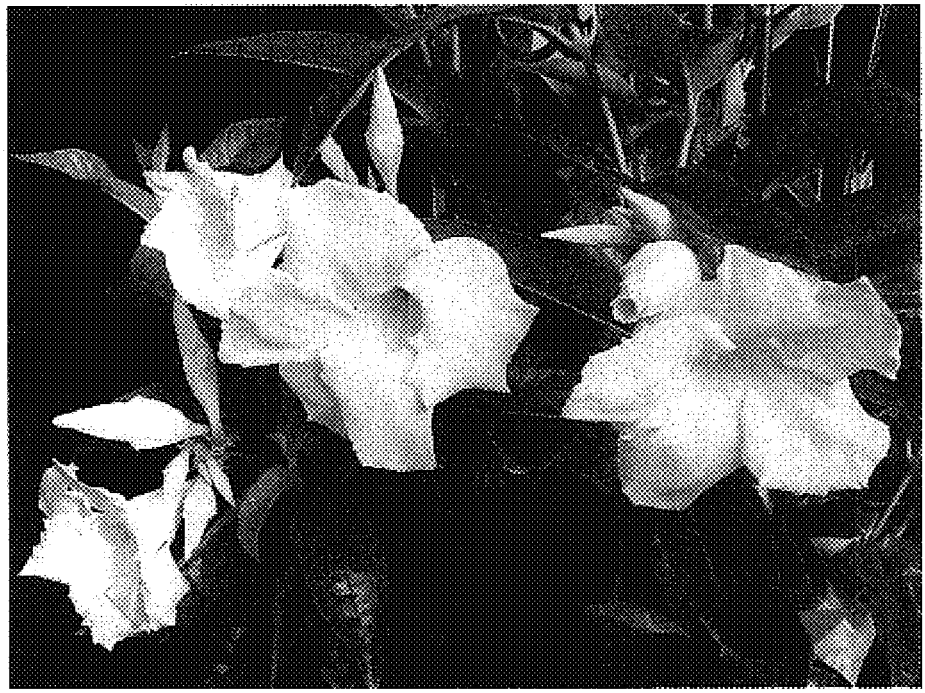

* * * * *